United States Patent
Roos et al.

(10) Patent No.: US 9,936,147 B2
(45) Date of Patent: Apr. 3, 2018

(54) LOW POWER STANDBY MODE IN WIRELESS IMAGERS

(71) Applicant: Varex Imaging Corporation, Salt Lake City, UT (US)

(72) Inventors: Gerhard Roos, Sunnyvale, CA (US); Nachiket Jugade, Salt Lake City, UT (US); Steve Wettstein, Lehi, UT (US); Cesar Proano, Palo Alto, CA (US)

(73) Assignee: Varex Imaging Corporation, Salt Lake City, UT (US)

( * ) Notice: Subject to any disclaimer, the term of this patent is extended or adjusted under 35 U.S.C. 154(b) by 298 days.

(21) Appl. No.: 14/229,534

(22) Filed: Mar. 28, 2014

(65) Prior Publication Data

US 2015/0276942 A1    Oct. 1, 2015

(51) Int. Cl.
*H01L 27/146* (2006.01)
*H04N 5/32* (2006.01)
*H04N 5/232* (2006.01)
*H02J 9/00* (2006.01)

(52) U.S. Cl.
CPC ........... *H04N 5/32* (2013.01); *H04N 5/23241* (2013.01); *A61B 2560/0209* (2013.01); *H02J 9/005* (2013.01)

(58) Field of Classification Search
CPC .................... A61B 2560/0209; H02J 9/005

USPC .......................................................... 378/102
See application file for complete search history.

(56) References Cited

U.S. PATENT DOCUMENTS

| 8,983,036 B2 * | 3/2015 | Tredwell | G01T 1/2018 |
| | | | 250/370.01 |
| 2004/0104709 A1 | 6/2004 | Yamaji et al. | |
| 2009/0232278 A1 * | 9/2009 | Ohara | A61B 6/00 |
| | | | 378/116 |
| 2011/0317809 A1 * | 12/2011 | Eguchi | A61B 6/4233 |
| | | | 378/62 |

FOREIGN PATENT DOCUMENTS

| JP | 2000347330 | 12/2000 |
| JP | 4360938 | 11/2009 |
| WO | 0143153 | 6/2001 |

* cited by examiner

*Primary Examiner* — Kenneth J Malkowski

(57) ABSTRACT

This invention describes a novel solution to conserve battery and to overcome cold-start artifacts by maintaining the pixel charge traps at a stable value at all times. The design of NIP photodiode and TFT combination requires very low current (in order of hundreds of µA) to stay biased at all times. This allows the pixel charge traps to be easily maintained at a stable value with low power consumption. Power consumption is kept at a minimum by keeping all panel electronics off and only the pixels biased. In addition, keeping the pixels biased helps to overcome the cold-start artifact in the very first image.

17 Claims, 6 Drawing Sheets

Exemplary Computer System 600

LOW POWER STANDBY MODE IN WIRELESS IMAGERS

BACKGROUND OF THE INVENTION

Radiology is the branch of medical science dealing with medical imaging for the purpose of diagnosis and treatment. The practice of radiology often involves the usage of X-ray machines or other radiation devices to perform the diagnosis or administer the treatment. Other practices of radiology employ techniques that do not involve radiation, such as magnetic resonance imaging (MRI) and ultrasound. Within the medical field, radiology can refer to two sub-fields, diagnostic radiology and therapeutic radiology. Diagnostic radiology is concerned with the use of various imaging modalities to aid in the diagnosis of disease or condition. Therapeutic radiology or radiation oncology uses radiation to treat diseases such as cancer through the application of radiation to targeted areas.

In diagnostic radiology, a typical configuration for a radiology device includes a radiation source used to emit the irradiating particles (e.g., X-rays) and one or more imaging devices corresponding to the radiation source. The particles are directed towards a target volume (i.e., a patient) situated between the source and imaging device(s), with the imaging device(s) being positioned to collect incoming radiation that passes through the target volume. The beams collected by the imagers are subsequently used to generate one or more images of the targeted volume.

The imagers used for X-ray often comprise integrated circuits in the form of amorphous-silicon (a-Si) thin film transistor (TFT) arrays. Traditionally, these imagers are mounted at the end of one or more "arms" attached to a gantry shared with the radiation source. FIG. 1 depicts a conventional digital imaging system 100 which may be used to capture images to assist a physician in making accurate diagnoses. As depicted, the digital imaging system 100 of FIG. 1 depicts radiation source 110 with a corresponding detector 120 mounted on a robotic arm 130. These arms may be implemented as robotic, programmable arms capable of automated moving and/or rotating the imager along one or more axes according to pre-planned routes. Along with providing support and stability, the arm also provides a housing for power and data transmission channels (e.g., cables) between the imager and the rest of the gantry. Recently, imagers have been developed to transmit radiographic data wirelessly. For increased portability, battery powered wireless flat panel imagers have been developed. However, while extending certain advantages, the shift from mains supplied power sources to battery powered sources also brings with it a new set of issues.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

An embodiment of the present invention proposes a more efficient technique for conserving power using limited power sourced wireless imagers while remaining capable of generating high quality images. This invention describes a novel solution to conserve battery and to overcome cold-start artifacts by maintaining the pixel charge traps at a stable value at all times. The design of NIP photodiode and TFT combination requires very low current (in order of hundreds of µA) to stay biased at all times. This allows the pixel charge traps to be easily maintained at a stable value with low power consumption. Power consumption is kept at a minimum by keeping all panel electronics off and only the pixels biased. In addition, keeping the pixels biased helps to overcome the cold-start artifact in the very first image.

According to an aspect of the present claimed subject matter, a system is provided that includes a wireless flat panel detector consisting of an array of charge storage devices connected to a read amplifier, row drivers, and a bias supply. In an embodiment, each charge storage device consists of a photodiode for storing charge and a thin-film-transistor switch that controls the flow of charge from the photodiode to the read amplifier. According to such embodiments, the drivers control the operation of the switches (based on receiving triggering instructions) to close or allow the flow of charge to a read amplifier during a scan-out. When the wireless flat panel detector is idle or in otherwise a low power state, the bias supply provides a reverse bias voltage to the charge storage devices in order to maintain a stable voltage level.

According to another aspect of the present claimed subject matter, a method is provided for adjusting power states of various components in the wireless flat panel detector during periods of idle or non-operation. According to an embodiment, a change in the power state from an active or normal operating level of the wireless flat panel detector to an idle or low power operating level is detected. Based on the detected change, the operating power levels of imaging components and wireless transmission modules are also adjusted (decreased) accordingly, and the supply of a reverse bias voltage to the charge storage devices is maintained to keep the charge storage devices at a stable voltage level.

According to yet another aspect, a method is provided for adjusting power states of various components in the wireless flat panel detector when transitioning out of periods of idle or non-operation. According to an embodiment, a change in the power state from an idle or low power operating level of the wireless flat panel detector to an active power state is detected. Based on the detected change, the operating power levels of imaging components and wireless transmission modules are also adjusted (increased) in response, and the supply of a reverse bias voltage to the charge storage devices is maintained when the normal supply of power is resumed.

BRIEF DESCRIPTION OF THE DRAWINGS

The accompanying drawings are incorporated in and form a part of this specification. The drawings illustrate embodiments. Together with the description, the drawings serve to explain the principles of the embodiments.

DETAILED DESCRIPTION

Figure 1:
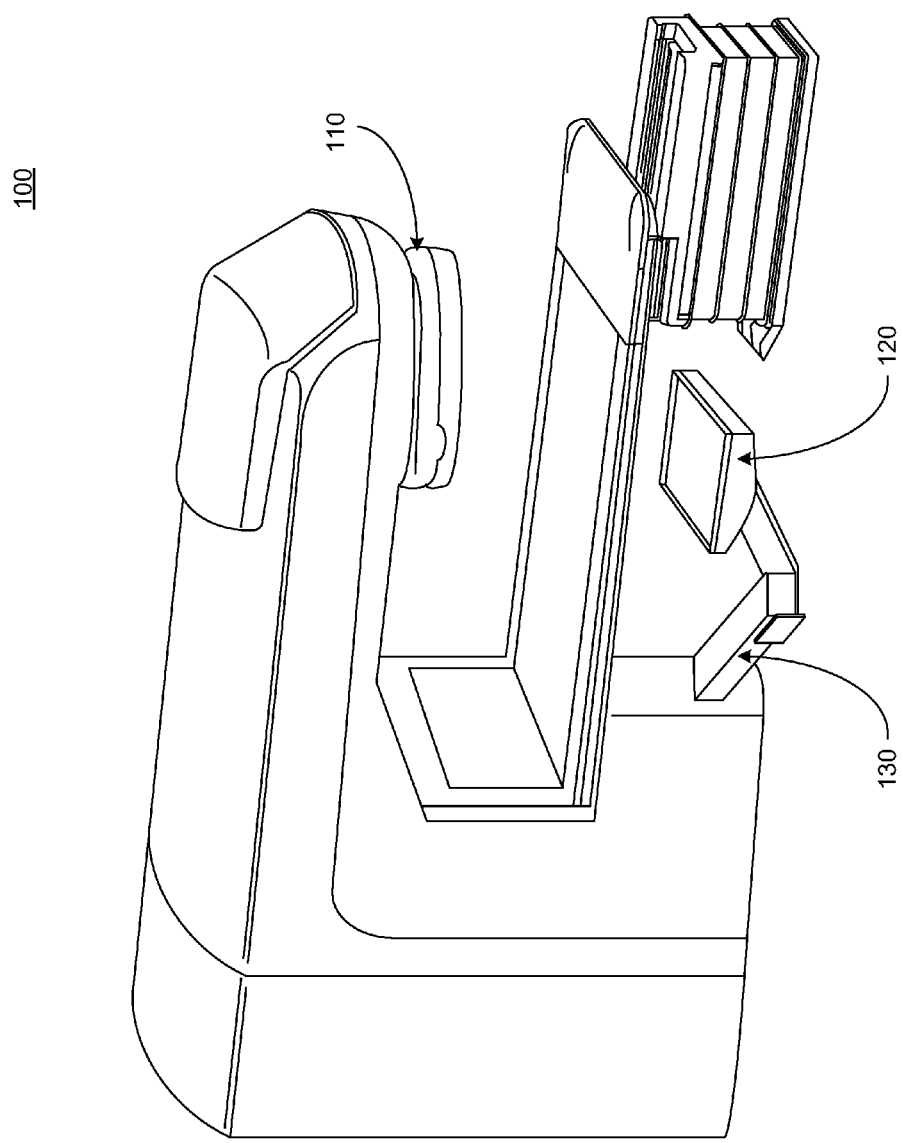
FIG. 1 depicts a conventional radiographic imaging device, in accordance with various embodiments of the present invention.

Reference will now be made in detail to the preferred embodiments of the claimed subject matter, a method and system for the use of a reputation service provider, examples of which are illustrated in the accompanying drawings. While the claimed subject matter will be described in conjunction with the preferred embodiments, it will be understood that they are not intended to be limit to these embodiments. On the contrary, the claimed subject matter is intended to cover alternatives, modifications and equivalents, which may be included within the spirit and scope as defined by the appended claims.

Furthermore, in the following detailed descriptions of embodiments of the claimed subject matter, numerous specific details are set forth in order to provide a thorough understanding of the claimed subject matter. However, it will be recognized by one of ordinary skill in the art that the claimed subject matter may be practiced without these specific details. In other instances, well known methods, procedures, components, and circuits have not been described in detail as not to unnecessarily obscure aspects of the claimed subject matter.

Some portions of the detailed descriptions which follow are presented in terms of procedures, steps, logic blocks, processing, and other symbolic representations of operations on data bits that can be performed on computer memory. These descriptions and representations are the means used by those skilled in the data processing arts to most effectively convey the substance of their work to others skilled in the art. A procedure, computer generated step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present claimed subject matter, discussions utilizing terms such as "storing," "creating," "protecting," "receiving," "encrypting," "decrypting," "destroying," or the like, refer to the action and processes of a computer system or integrated circuit, or similar electronic computing device, including an embedded system, that manipulates and transforms data represented as physical (electronic) quantities within the computer system's registers and memories into other data similarly represented as physical quantities within the computer system memories or registers or other such information storage, transmission or display devices.

Embodiments of the claimed subject matter are directed to solutions for providing power conservation techniques in a wireless imager while maintaining high quality imaging capability. According to an embodiment, the wireless imager may be implemented as a radiographic flat panel detector with a specific pixel design, with each pixel being formed by a combination of NIP type photodiode (N-type, intrinsic, P-Type semiconductor formation) and TFT switch.

Digital Imaging System

Figure 2:
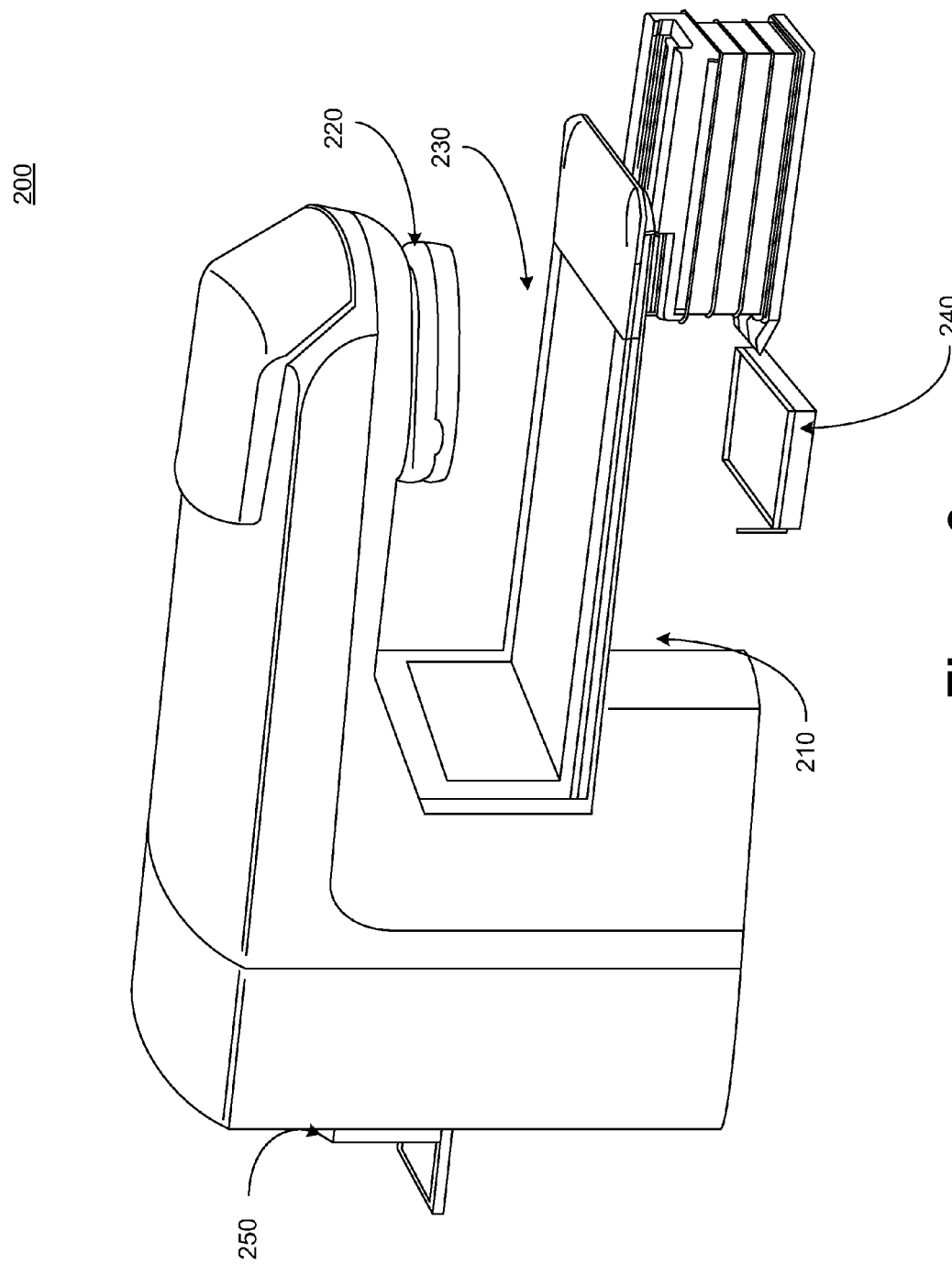
FIG. 2 depicts a radiographic imaging device with a wireless detector, in accordance with various embodiments of the present invention.

FIG. 2 represents a digital imaging system 200 according to embodiments of the claimed subject matter. The digital imaging systems such as those depicted in FIG. 2 may include one or more radiation sources 220. For example, the digital imaging system 200 of FIG. 2 may be implemented as a kilovolt (KV) radiation source and/or a megavolt (MV) radiation source, with a corresponding number of detectors. According to an embodiment, one or more of the detectors may be implemented as wireless flat panel imagers 240. In alternate embodiments, the one or more of the radiation sources may be operable to generate both KV and MV radiation. Likewise, a single imager may be used to receive radiation from both sources. According to these embodiments, one or more of the radiation and/or imagers may not be present. In still further embodiments, the imaging system 200 may also include a communicatively coupled computing device 250 for performing image processing and/or controlling and manipulating the digital imaging system 200.

Radiation energy, such as X-rays, produced by the radiation source 220 travel through a volume to be imaged (positioned on surface 230, for example) and are detected (i.e., received) by the imager 240. According to one embodiment, the particles received in the imager 240 generate electron-hole-pairs in an array of charge storage devices in the imager, accumulating charge which is stored in an intrinsic capacitor of the charge storage devices. The accumulated charge carriers are subsequently fed (e.g., pixel by pixel) into a read out circuit. In an embodiment, data corresponding to radiation energy received for each radiographic image are transmitted wirelessly to a corresponding image processing device 250. In an embodiment the imager 240 comprises a memory, and the imager 240 is able to store data corresponding to a number of radiographic images, and to subsequently wirelessly transmit these data to the image processing device 250. In a further embodiment the memory of imager 240 is substantially radiation-hardened, using substrates and/or logical methods known to those skilled in the art.

The corresponding image processing device 250 obtains image data from the imager 240 and prepares a diagnostic image on a display corresponding to the arrangement of the detection sites in the imager. The image may be subsequently displayed on a computer monitor, or stored in memory or on a tangible computer readable medium. The images may also be used for verifying and/or adjusting patient positioning on a therapy machine, for example. Additionally, the imaging system may also be used as a 2-dimensional dose measuring device (Dosimetry), which allows the verification of the accurate dose delivery of the therapy machine. In even more advanced applications the captured signals by the imaging system can be used to calculate the dose deposited in the patient.

Figure 3:
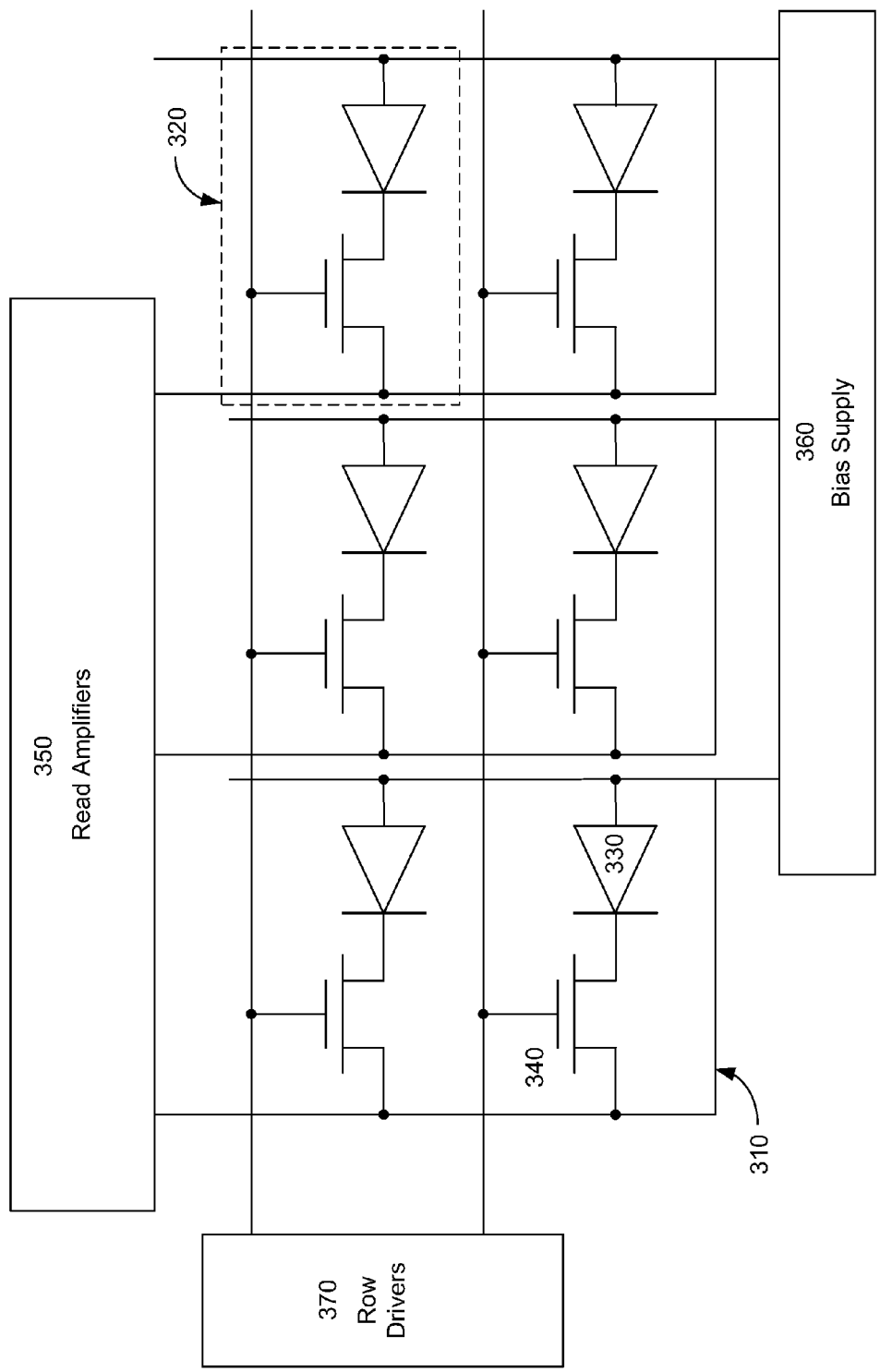
FIG. 3 depicts an exemplary sensor array in a wireless detector, in accordance with various embodiments of the present invention.

FIG. 3 depicts an exemplary configuration of a flat panel imager 300, such as flat panel imager 240 described in FIG. 2. According to an embodiment, a flat panel imager depicted in FIG. 2 may be implemented as a sensor panel consisting of an array 310 of charge storage devices configured to perform X-ray conversion and real-time imaging. Each pixel that constitutes an image generated using the imager 300 may correspond to a specific charge storage device (e.g., charge storage device 320). A charge storage device may, according to various embodiments, be implemented as a capacitor in photoconductor imagers or as a photodiode in panels used with scintillators placed in front of the flat panel detector. Charge storage devices are used to accumulate charge generated by the absorption of X-ray particles and to provide it row by row (or column by column) during scan-outs to charge read amplifiers 350. In embodiments using scintillators, the scintillators act as an absorber of X-rays. The scintillators convert the absorbed X-ray particles to visible light photons at energies that the photodiodes are able to convert to charge carriers. An imager may also include one or more switches used to control (i.e., permit or prevent) the charge from flowing out. These switches may be implemented as, for example, a single diode, a diode pair or a thin-film transistor (TFT).

A specific embodiment of an imager panel may, for example, consist of the photodiode-scintillator combination of charge storage units 330 and TFT switches 340. According to these embodiments, each of the photodiodes are reverse-biased during operation by an external voltage applied to them (e.g., from Bias Supply 360). While the TFT switches are off, charge generated by light from the scintillator accumulates in the diodes. When a readout is requested, a line (row, column) is energized (via Row Drivers 370 for example) to turn on the switches in that line. According to an embodiment, the charge from all of the photodiodes in the selected line flows out through all of the data lines simultaneously. In large arrays, this produces several thousand signals that must all be read at the same time.

In the interest of prolonging battery life and extending time between recharges, the imager may enter a low power or idle state during periods of inactivity or non-use. However, during such periods, the photodiodes will continue to accumulate charge from ambient light. Over time, the accumulated charge can reach non-trivial levels and if left unchecked, may distort or compromise images taken with the collected charge. To avoid this, previous solutions will continuously refresh the charge accumulated on the photodiode periodically, usually at specific intervals, even when the detector is idle and waiting for a trigger to be read out. The result of the continuous refresh cycles ensures that any accumulated charge in the photodiode is flushed out prior to an asynchronous X-ray exposure trigger. If a refresh prior to an asynchronous X-ray exposure trigger does not occur, then undesirable side-effects like lag and ghosting may occur in the displayed X-ray exposed image. This may lead to incorrect image data for the patient or other undesirable effects.

However, continuously refreshing the photodiodes also requires higher power consumption, which naturally leads to significantly faster power consumption rates and quicker exhaustion of the battery's charge. According to embodiments of the present claimed subject matter, in order to conserve battery, panel electronics may be shut off during the period when the power state of the imager is in its idle state (i.e., when no read-out trigger was initiated). In an embodiment, only the wireless radio module is powered on at all times, in order to respond to any trigger initiations transmitted from the imaging system, for example. However, simply shutting off all the electronics may cause the very first image after a cold start to exhibit undesirable behavior, such as very high pixel counts due to a slow decay of photodiode charge. The pixel counts settle over time as the photodiode charge traps return to a stable value; after which the image quality achieves consistency.

Due to the radiographic nature of the detector, it is extremely critical to get a high quality first image immediately after a cold-start. This invention describes a novel solution to conserve battery and to overcome cold-start artifacts by maintaining the pixel charge traps at a stable value at all times. The design of NIP photodiode and TFT combination requires very low current (in order of hundreds of µA) to stay biased at all times. This allows the pixel charge traps to be easily maintained at a stable value with low power consumption. Power consumption is kept at a minimum by keeping all panel electronics off and only the pixels biased. In addition, keeping the pixels biased helps to overcome the cold-start artifact in the very first image.

According to these embodiments, the power state of the wireless flat panel detector may be manually adjusted (e.g., via a user interface on the wireless flat panel detector). In alternate embodiments, the wireless radio module may be kept at a low power state capable of receiving data transmissions from a wireless transceiver in the imaging system. These data transmissions may act as triggers and/or interrupts in an operating system of the wireless flat panel device to adjust the power state of the flat panel device (e.g., by restoring the operating level to a normal active operating level from a low power idle state or vice versa).

Figure 4:
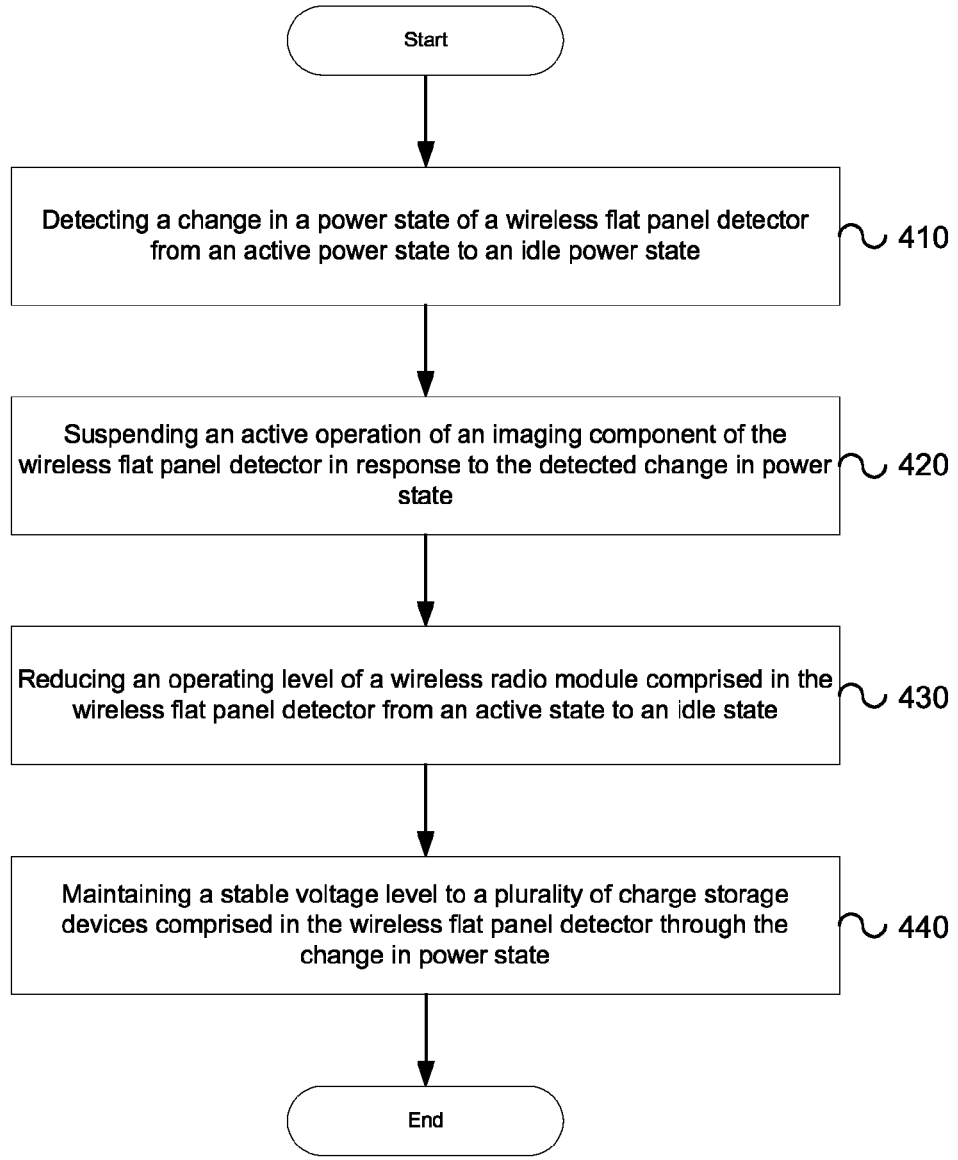
FIG. 4 depicts a flowchart of an exemplary process of changing an operating power state of a wireless imager in a power state to a lower power state, in accordance with various embodiments of the present invention.

FIG. 4 depicts a flowchart 400 of such a process of changing an operating power state of a wireless imager in a power state to a lower power state, in accordance with various embodiments of the present invention. Steps 410-440 describe exemplary steps comprising the process depicted in flowchart 400 in accordance with the various embodiments herein described. In one embodiment, the flowchart 400 is implemented as computer-executable instructions stored in a computer-readable medium and performed by a processor in a wireless flat panel detector.

At step 410, a change in the power state of the wireless flat panel detector is detected. In one embodiment, the change detected corresponds from a change in the power state from an active operating power state to an idle or lower power state. The change may be detected based on receiving a trigger transmitted from a primary operating station (e.g., a computing device corresponding to the radiographic imaging device corresponding to the wireless flat panel detector). The trigger may be submitted in response to the completion of an imaging task, manually triggered by a user of the imaging device, e.g., in anticipation of a period of low or non imaging activity, or based on pre-determined triggers (e.g., to correspond to customary non-operational hours), for example. In further embodiments, the change in the operating power state may be determined when no imaging activity has been performed with the wireless detector for a period of time exceeding a pre-determined threshold.

At step 420, the active operation of imaging components in the wireless flat panel detector is suspended when the change in power state to a low power or idle power state is detected at step 410. In one or more embodiments, the low power state may correspond to sleep or hibernation power states of other computing devices, wherein processes and usage (consumption) of processing resources (memory accesses, processing) may be suspended and/or slowed. In an embodiment, the operating level of the imaging module (e.g., the row drivers, read amplifiers, scintillator, sensor array, etc.) in the wireless flat panel detector may be reduced and/or completely suspended.

At step 430, the wireless radio module comprised in the wireless flat panel detector will also experience a reduction in power state and operating level upon the detection at step 410 of the change in power state of the imaging device. In an embodiment, operation of the wireless radio module may be suspended completely. In alternate embodiments, the wireless radio module may be reduced to a lowest power state that is still capable of receiving wireless data (e.g., a trigger or interrupt) from the primary operating station. According to such embodiments, the wireless radio module may receive and buffer transmitted wireless data from the primary operating station. At periodic intervals, the operating system of the wireless flat panel detector may query the wireless radio module to determine whether data (e.g., a trigger) has been received, which may signal a resumption of active operation. If no trigger has been received, the low power state is maintained until the next query interval.

At step 440, a supply of voltage to the charge storage devices sufficient to hold the charge storage devices at a stable voltage level is maintained. According to one or more embodiments, the voltage level is the lowest voltage sufficient to keep the charge storage devices reverse biased relative to a normal operating level. In one or more embodiments, the supply of voltage is provided by a power supply (e.g., a battery power source) in the wireless flat panel detector. While presented in a sequence, steps 420, 430, and 440 may be performed in any order, or substantially simultaneously upon the detection of the change in power state at step 410. By keeping the charge storage devices reverse biased, cold-start artifacts in images generated after periods of idleness can be avoided.

Figure 5:
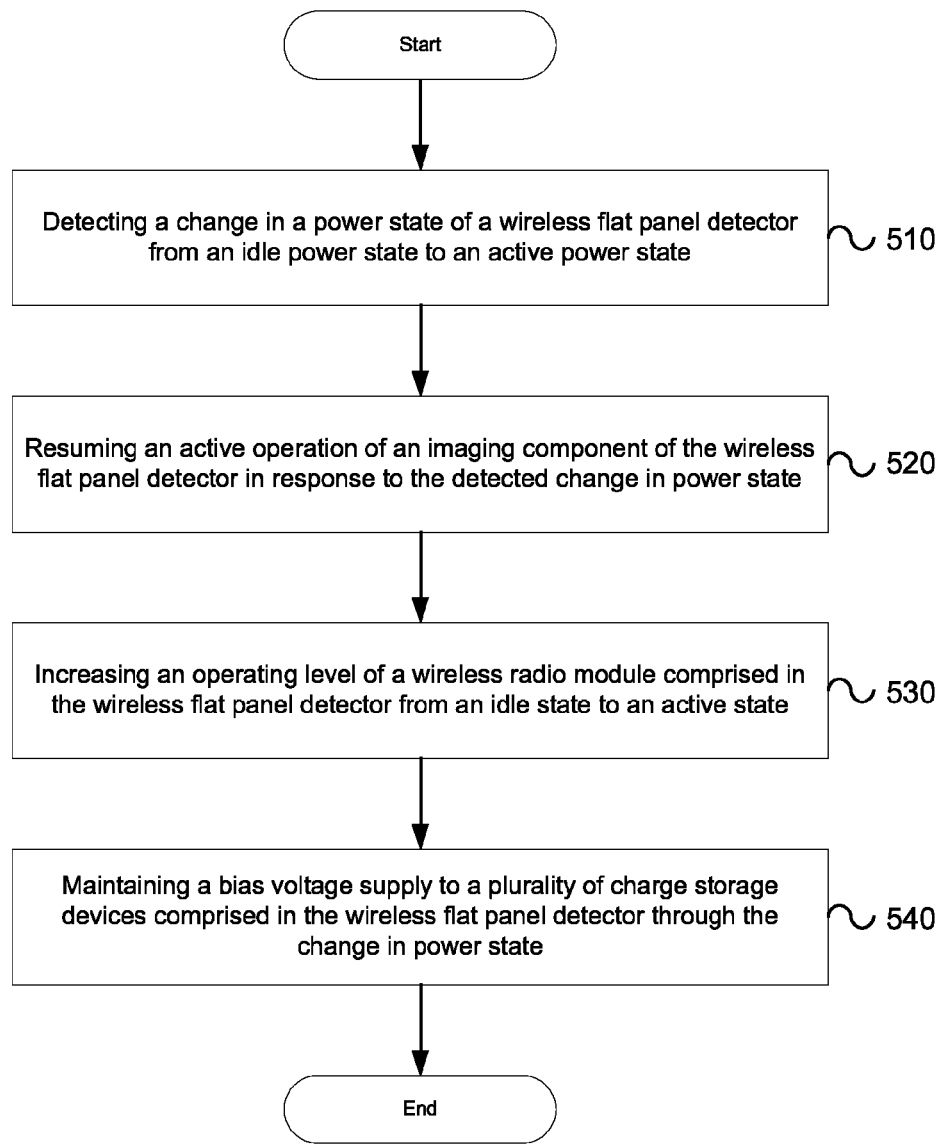
FIG. 5 depicts a flowchart of an exemplary process of changing an operating power state of a wireless imager in a low power state to a higher power state, in accordance with various embodiments of the present invention.

FIG. 5 depicts a flowchart 500 of an exemplary process of changing an operating power state of a wireless imager in a low power state to a higher power state, in accordance with various embodiments of the present invention. Steps 510-540 describe exemplary steps comprising the process depicted in flowchart 500 in accordance with the various embodiments herein described. In one embodiment, the flowchart 500 is implemented as computer-executable instructions stored in a computer-readable medium and performed by a processor in a wireless flat panel detector.

The process depicted in flowchart 500 substantially mirrors the process described in flowchart 400, and describes the process performed when a wireless flat panel detector reverts from a low power state to a normal or active power state. At step 510 a change in the power state of the wireless flat panel detector is detected. In one embodiment, the change detected corresponds from a change in the power state from an idle or low power operating state to a normal, active power state. The change may be detected based on receiving a trigger transmitted from a primary operating station (e.g., a computing device corresponding to the radiographic imaging device corresponding to the wireless flat panel detector). The trigger may be submitted in response to the initiation of an imaging task, manually triggered by a user of the imaging device, e.g., in anticipation of an imaging task or in preparation of imaging activity, or based on pre-programmed triggers (e.g., to correspond to normal operating hours), for example.

At step 520, the active operation of imaging components in the wireless flat panel detector is resumed when the change in power state to an active or high power state is detected at step 510. In one or more embodiments, the active power state may correspond to normal power states consistent with an active operation of the wireless flat panel detector, wherein processes and usage (consumption) of processing resources (memory accesses, processing) are consistent with normal operating levels.

At step 530, the power state of a wireless radio module comprised in the wireless flat panel detector will also experience an increase in power state and operating level upon the detection at step 510 of the change in power state of the imaging device. In an embodiment, the wireless radio module may resume active transmission with the primary operating station (e.g., to receive instructions for read-out or operation, or to transmit image data).

At step 540, a bias supply of voltage to the charge storage devices (provided while the wireless detector is in a low power or idle power state) is maintained. According to one or more embodiments, the bias supply is maintained by the power supply at a voltage level used during normal or active operation of the wireless flat panel detector. According to these embodiments, the supply of voltage is provided by a power supply (e.g., a battery power source) in the wireless flat panel detector. While presented in a sequence, steps 520, 530, and 540 may be performed in any order, or substantially simultaneously upon the detection of the change in power state at step 510. According to the processes depicted in flowcharts 400 and 500, cold-start artifacts in images generated after periods of idleness can be avoided by keeping the charge storage devices reverse biased during non-operation, and ceasing the supply of the reverse bias voltage upon the resumption of normal operating power levels.

Exemplary Computer System

Figure 6:
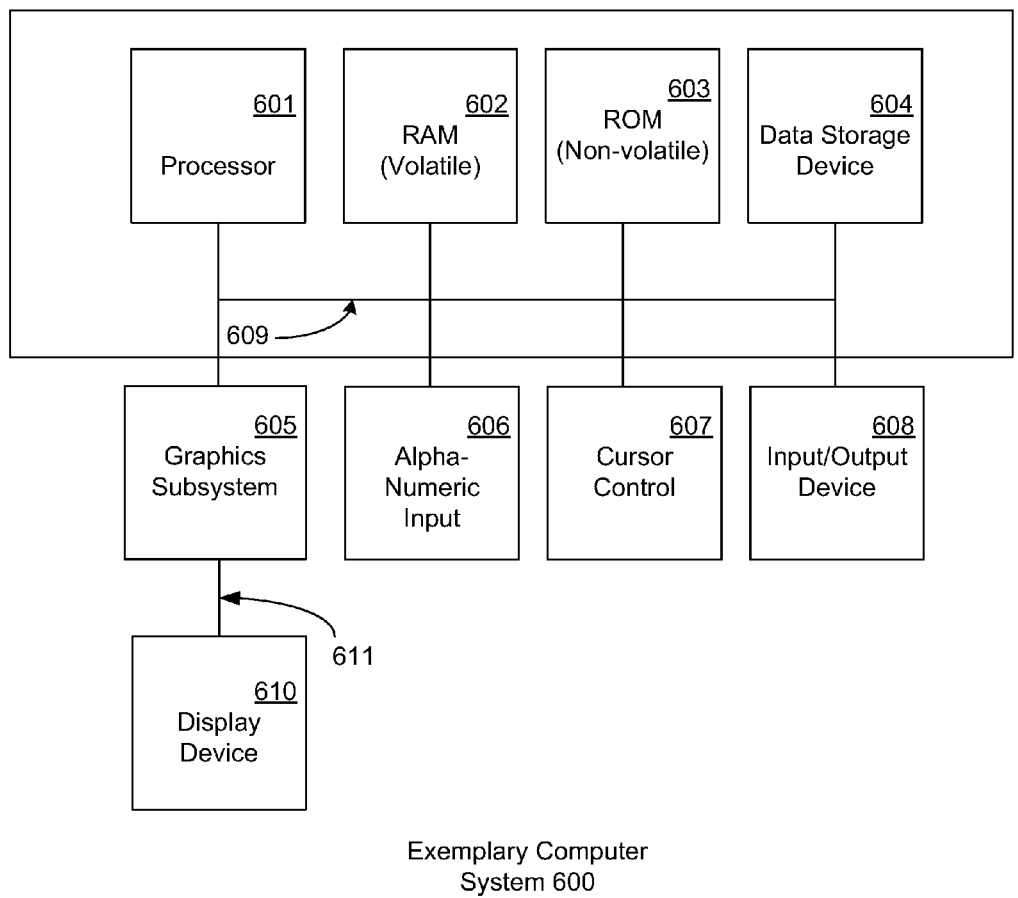
FIG. 6 depicts an exemplary computing device, in accordance with various embodiments of the present invention.

As presented in FIG. 6, an exemplary system 600 upon which embodiments of the present invention may be implemented includes a general purpose computing system environment, such as image processing device 250 described above with respect to FIG. 2. Exemplary computer system 600 may also be comprised as a portion of the wireless detector (240 in FIG. 2), most prominently the portion of the wireless detector configured to provide wireless data transmission functionality. In its most basic configuration, computing system 600 typically includes at least one processing unit 601 and memory, and an address/data bus 609 (or other interface) for communicating information. Depending on the exact configuration and type of computing system environment, memory may be volatile (such as RAM 602), non-volatile (such as ROM 603, flash memory, etc.) or some combination of the two.

The computer system 600 (of image processing device 250 for example) may also comprise an optional graphics subsystem 605 for presenting information to the radiologist or other user, e.g., by displaying information on an attached display device 610, connected by a video cable 611. According to embodiments of the present claimed invention, the graphics subsystem 605 may be coupled directly to the display device 610 through the video cable 611. A graphical user interface of an application for displaying images generated by a medical imaging device described above with respect to FIG. 2, and executing in the computer system 600 may be generated in the graphics subsystem 605, for example, and displayed to the user in the display device 610. In alternate embodiments, display device 610 may be integrated into the computing system (e.g., a laptop or netbook display panel) and will not require a video cable 611. In one embodiment, the processing of the image data acquired in the detectors 130, 140 to generate an image may be performed, in whole or in part, by graphics subsystem 605 in conjunction with the processor 601 and memory 602, with any resulting output displayed in attached display device 610.

Additionally, computing system 600 may also have additional features/functionality. For example, computing system 600 may also include additional storage (removable and/or non-removable) including, but not limited to, magnetic or optical disks or tape. Such additional storage is illustrated in FIG. 6 by data storage device 607. Computer storage media includes volatile and nonvolatile, removable and non-removable media implemented in any method or technology for storage of information such as computer readable instructions, data structures, program modules or other data. RAM 602, ROM 603, and data storage device 607 are all examples of computer storage media.

Computer system 600 also comprises an optional alphanumeric input device 606, an optional cursor control or directing device 607, and one or more signal communication interfaces (input/output devices, e.g., a network interface card) 609. Optional alphanumeric input device 606 can communicate information and command selections to central processor 601. Optional cursor control or directing device 607 is coupled to bus 609 for communicating user input information and command selections to central processor 601. Signal communication interface (input/output device) 609, also coupled to bus 609, can be a serial port. Communication interface 609 may also include wireless communication mechanisms. Using communication interface 609, computer system 600 can be communicatively coupled to other computer systems over a communication network such as the Internet or an intranet (e.g., a local area network), or can receive data (e.g., a digital television signal). The communication interface 609 may also be used to transmit data wirelessly between a computing system disposed in the wireless detector 240 and a separate computing system disposed in the image processing device 250.

In the foregoing specification, embodiments have been described with reference to numerous specific details that may vary from implementation to implementation. Thus, the sole and exclusive indicator of what is the invention, and is intended by the applicant to be the invention, is the set of claims that issue from this application, in the specific form in which such claims issue, including any subsequent correction. Hence, no limitation, element, property, feature, advantage, or attribute that is not expressly recited in a claim should limit the scope of such claim in any way. Accordingly, the specification and drawings are to be regarded in an illustrative rather than a restrictive sense.

What is claimed is:

1. A wireless flat panel detector comprising:
   a plurality of charge storage devices configured to absorb radiation from a radiation source;
   a plurality of imaging components configured to generate image data from the radiation absorbed in the plurality of charge storage devices;
   a wireless radio module operable for wirelessly transmitting data with the radiation source;
   a battery configured to supply power to the wireless flat panel detector,
      wherein, the battery is configured to supply power to the wireless radio module and a bias voltage to the plurality of charge storage devices to keep the plurality of charge storage devices at a stable voltage level when the wireless flat panel detector is in an idle power state and wherein power is not otherwise supplied to the plurality of imaging components while the wireless flat panel detector is in the idle power state,
      further wherein, the stable voltage level comprises a reverse bias voltage level relative to a normal operating voltage level of the plurality of charge storage devices; and
   a processor operable for executing instructions configured to periodically query the wireless radio module while the wireless flat panel detector is in the idle power state to determine whether a trigger has been received to signal a resumption of active operation.

2. The wireless flat panel detector according to claim 1, wherein a charge storage device of the plurality of charge storage devices comprises:
   a charge storage unit comprising at least one element from the group consisting of: a capacitor, and a photodiode with a scintillator; and
   a switch comprising at least one switch from the group consisting of: a single diode, a diode pair, and a thin-film transistor (TFT) switch.

3. The wireless flat panel detector according to claim 1, further comprising:
   a plurality of charge amplifiers configured to receive and amplify charge received in the plurality of charge storage devices.

4. The wireless flat panel detector according to claim 1, wherein the plurality of charge storage devices are arranged as an array of charge storage devices.

5. The wireless flat panel detector according to claim 4, wherein the array of charge storage devices comprises a two dimensional array arranged in a plurality of rows and columns.

6. The wireless flat panel detector according to claim 5, further comprising a plurality of drivers, a driver of the plurality of drivers corresponding to a row or a column of the two dimensional array of charge storage devices and configured to control a state of a plurality of thin-film transistor (TFT) switches of the charge storage devices in the row or column corresponding to the driver.

7. The wireless flat panel detector according to claim 1, wherein each charge storage device of the plurality of charge storage devices comprises an amorphous silicon diode.

8. The wireless flat panel detector according to claim 7, wherein the amorphous silicon diode comprises an N-type material, intrinsic, and P-type material (NIP) diode.

9. The wireless flat panel detector according to claim 1, wherein the trigger comprises at least one event from the group consisting of: a completion of an imaging task, a manual trigger provided by a user of the wireless flat panel detector, and a determination of no imaging activity having been performed with the wireless flat panel detector for a period of time exceeding a pre-determined threshold.

10. A method of operating a wireless flat panel detector, the method comprising:
   detecting a change in a power state of a wireless flat panel detector from an active power state to an idle power state;
   suspending an active operation of an imaging component of the wireless flat panel detector in response to the detected change in power state;
   reducing an operating level of a wireless radio module comprised in the wireless flat panel detector from an active state to an idle state;
   maintaining a stable voltage level at a plurality of charge storage devices comprised in the wireless flat panel detector through the change in power state, the stable voltage level comprising a reverse bias voltage relative to a normal operating voltage level in the plurality of charge storage devices,
      wherein the plurality of charge storage devices is configured to absorb radiation from a radiation source corresponding to the wireless flat panel detector; and
   periodically querying the wireless radio module comprised in the wireless flat panel detector while the wireless flat panel detector is in the idle state to determine whether a trigger has been received to signal a resumption of the active state.

11. The method according to claim 10, wherein suspending the active operation of the imaging component comprises substantially reducing a rate at which power is consumed by the imaging component relative to a rate at which power is consumed by the imaging component when the wireless flat panel detector is in the active power state.

12. The method according to claim 10, wherein the supply of power to the wireless radio module and the stable voltage level are provided by a battery source comprised in the wireless flat panel detector.

13. The method according to claim 10, wherein the change in power state of the wireless flat panel detector from the active power state to the idle power state corresponds to at least one operation from the group consisting of:
 detecting a change in a primary power source of the wireless flat panel detector from a main power supply to a battery power source;
 determining an idle period of time of the wireless flat panel detector exceeding a pre-determined threshold; and
 receiving a command from a user corresponding to a reduced power state of the wireless flat panel detector.

14. A method of operating a wireless flat panel detector, the method comprising:
 receiving a trigger event, wherein receiving the trigger event comprises periodically querying a wireless radio module comprised in the wireless flat panel detector while the wireless flat panel detector is in an idle state to determine the trigger event has been received;
 initiating a change in a power state of a wireless flat panel detector from an idle power state to an active power state in response to the trigger event;
 resuming an active operation of an imaging component of the wireless flat panel detector in response to the detected change in power state;
 increasing an operating level of the wireless radio module comprised in the wireless flat panel detector from the idle state to an active state; and
 maintaining a stable voltage at a plurality of charge storage devices comprised in the wireless flat panel detector through the change in power state, the stable voltage comprising a reverse bias voltage relative to a normal operating voltage level in the plurality of charge storage devices during the active state,
 wherein the plurality of charge storage devices are configured to absorb radiation from a radiation source corresponding to the wireless flat panel detector.

15. The method according to claim 14, wherein resuming the active operation of the imaging component comprises substantially increasing a rate at which power is consumed by the imaging component relative to a rate at which power is consumed by the imaging component when the wireless flat panel detector is in the idle power state.

16. The method according to claim 14, wherein the supply of power to the wireless radio module and the stable voltage are provided by a battery source comprised in the wireless flat panel detector.

17. The method according to claim 14, wherein the change in power state of the wireless flat panel detector from the idle power state to the active power state corresponds to an operation.

* * * * *